(12) United States Patent  (10) Patent No.: US 7,607,432 B2
Sullivan  (45) Date of Patent: *Oct. 27, 2009

(54) APPARATUS AND METHOD FOR THE TREATMENT OF AN UPPER AIRWAY FLOW LIMITATION

(75) Inventor: Colin Sullivan, Sydney (AU)

(73) Assignee: Australian Centre for Advanced Medical Technology Ltd, Sydney (AU)

( * ) Notice: Subject to any disclaimer, the term of this patent is extended or adjusted under 35 U.S.C. 154(b) by 368 days.

This patent is subject to a terminal disclaimer.

(21) Appl. No.: 11/373,125

(22) Filed: Mar. 13, 2006

(65) Prior Publication Data

US 2006/0150975 A1  Jul. 13, 2006

Related U.S. Application Data

(63) Continuation of application No. 09/959,303, filed as application No. PCT/AU00/00370 on Apr. 26, 2000, now Pat. No. 7,011,087.

(30) Foreign Application Priority Data

Apr. 23, 1999 (AU) .................................. PP9964

(51) Int. Cl.
  *A61M 16/00* (2006.01)
  *A61M 15/00* (2006.01)
(52) U.S. Cl. .................... 128/200.24; 128/204.18; 128/204.23
(58) Field of Classification Search ............ 128/204.18, 128/204.21, 204.23; 600/529, 534
See application file for complete search history.

(56) References Cited

U.S. PATENT DOCUMENTS

| 4,146,885 A | 3/1979 | Lawson, Jr. |
| 4,320,766 A | 3/1982 | Alihanka et al. |
| 4,509,527 A | 4/1985 | Fraden |
| 4,657,026 A | 4/1987 | Tagg |
| 4,686,999 A | 8/1987 | Snyder |
| 4,830,008 A | 5/1989 | Meer |
| 4,848,360 A | 7/1989 | Palsgard et al. |
| 4,862,144 A | 8/1989 | Tao |
| 5,099,702 A | 3/1992 | French |
| 5,117,819 A | 6/1992 | Servidio et al. |
| 5,134,995 A | 8/1992 | Gruenke et al. |
| 5,148,802 A | 9/1992 | Sanders et al. |
| 5,199,424 A | 4/1993 | Sullivan et al. |
| 5,245,995 A | 9/1993 | Sullivan et al. |
| 5,259,373 A | 11/1993 | Gruenke et al. |
| 5,335,654 A | 8/1994 | Rapoport |
| 5,353,788 A | 10/1994 | Miles |
| 5,490,502 A | 2/1996 | Rapoport |
| 5,513,631 A | 5/1996 | McWilliams |
| 5,535,739 A | 7/1996 | Rapoport |
| 5,546,933 A | 8/1996 | Rapoport |

(Continued)

FOREIGN PATENT DOCUMENTS

EP  0 811 394 A1  12/1997

(Continued)

*Primary Examiner*—Justine R Yu
*Assistant Examiner*—Annette F Dixon (57) ABSTRACT

An apparatus and a method for the treatment of an upper airway flow limitation, the apparatus including a means to detect an interruption in an upper airway inspiratory flow rate of the patient and further including a treatment means which treats the upper airway flow limitation on detection of the interruption cycle.

47 Claims, 4 Drawing Sheets

U.S. PATENT DOCUMENTS

| | | | |
|---|---|---|---|
| 5,549,106 | A | 8/1996 | Gruenke et al. |
| 5,704,345 | A | 1/1998 | Berthon-Jones |
| 5,794,614 | A | 8/1998 | Gruenke et al. |
| 5,813,399 | A | 9/1998 | Isaza et al. |
| 5,845,636 | A | 12/1998 | Gruenke et al. |
| 5,884,622 | A | 3/1999 | Younes |
| 5,901,704 | A | 5/1999 | Estes et al. |
| 5,928,189 | A | 7/1999 | Phillips et al. |
| 5,989,193 | A | 11/1999 | Sullivan |
| 6,398,739 | B1 | 6/2002 | Sullivan |
| 6,443,907 | B1 | 9/2002 | Mansy et al. |
| 6,450,957 | B1 | 9/2002 | Yoshimi et al. |
| 6,454,724 | B1 | 9/2002 | Greene et al. |
| 6,468,234 | B1 | 10/2002 | Van der Loos et al. |
| 6,485,441 | B2 | 11/2002 | Woodward |
| 6,575,916 | B2 | 6/2003 | Halleck et al. |
| 6,661,240 | B1 | 12/2003 | Johnson et al. |
| 6,666,830 | B1 | 12/2003 | Lehrman et al. |
| 7,011,087 | B1 * | 3/2006 | Sullivan ................ 128/200.24 |

FOREIGN PATENT DOCUMENTS

| | | |
|---|---|---|
| WO | 92 11054 | 7/1992 |
| WO | 97 28838 | 8/1997 |

\* cited by examiner

APPARATUS AND METHOD FOR THE TREATMENT OF AN UPPER AIRWAY FLOW LIMITATION

CROSS-REFERENCE TO RELATED APPLICATIONS

The present application is a continuation of U.S. application Ser. No. 09/959,303, now U.S. Pat. No. 7,011,087, nationalized on Feb. 4, 2002, which application was the national stage under 35 U.S.C. 371 of PCT/AU00/00370, filed Apr. 26, 2000, and claiming priority from Australian application PP9964 filed Apr. 23, 1999, the entire contents of which is hereby incorporated by reference.

TECHNICAL FIELD

The present invention concerns an apparatus and method for the treatment of an upper airway flow limitation in a patient. In particular, the present invention concerns an apparatus and method of treating hypertension caused by pre-eclampsia.

BACKGROUND

Hypertension in pregnancy is associated with increased risk of foetal growth retardation and in severe cases can lead to both maternal and foetal problems. It is the major complication of pregnancy and is one of the three leading causes of maternal death.

Hypertension in pregnant women is either a chronic condition caused by a disease unrelated to pregnancy (essential or secondary hypertension), or caused by a pregnancy induced condition known as "pre-eclampsia" (also known as "pregnancy induced hypertension"). In the former condition, elevated blood pressure is the cardinal patho-physiological feature. In pre-eclampsia, the increased blood pressure is a sign of the underlying disorder and the impact of the two conditions and their management on the mother and foetus is quite different. An attempt to differentiate these two classes of patient has led to confusion in terminology worldwide.

The circadian blood pressure (BP) variation in normal pregnancy is similar to that of non-pregnant women, with the highest value being in the morning and the lowest around midnight. A similar pattern exists in pregnancy accompanied by chronic (essential) hypertension.

In contrast, in women with pre-eclampsia, the diurnal blood pressure pattern is reversed with the maximum blood pressure occurring at night.

Pre-eclampsia is a disease of the placenta with widespread systemic effects affecting maternal renal, cerebral, hepatic and/or clotting functions. The principal clinical features include hypertension, proteinuria and oedema with any or all of these present.

While there are generally agreed risk factors for pre-eclampsia, the precise causes and mechanisms remain unproved. In addition, there are no clear indicators that are useful in predicting the occurrence or the severity of the condition. There are no known effective preventative measures and although various techniques and medications are used to limit the symptoms (in particular the hypertension), the only definitive treatment is delivery of the baby, and removal of the diseased placenta.

Pre-eclampsia usually occurs after 20 weeks gestation and most frequently near term. Pre-eclampsia (and the hypertension associated with it) is a different medical condition to essential or secondary hypertension (e.g., as illustrated by the different diurnal characteristics). The methods used to manage patients with pre-eclampsia mainly consist of closely monitoring the patient and if necessary, controlling blood pressure with medication. In severe cases, additional medications are used to prevent convulsions (eclampsia).

It has been recognised that obstructive sleep apnea (OSA) is related to elevated blood pressure. The inventor has previously demonstrated the treatment of OSA by use of Continuous Positive Airway Pressure (CPAP), and in particular nasal-Continuous Positive Airway Pressure (nCPAP). It has also been demonstrated that partial airflow limitation (upper airway resistance syndrome "UARS") can cause elevations in blood pressure and that the blood pressure can be controlled by the use of CPAP, and in particular nCPAP. However patients with pre-eclampsia-induced hypertension may not display symptoms indicative of UARS. Accordingly, UARS symptoms in such a patient may be missed resulting in the hypertension caused by pre-eclampsia going untreated.

SUMMARY OF THE INVENTION

In a first aspect, the present invention consists in an apparatus for the treatment of an upper airway flow limitation in a patient, the apparatus including;

a means to detect at least one interruption cycle in an upper airway inspiratory flow rate of the patient wherein the interruption cycle is characterised by a decrease in upper airway inspiratory flow rate followed by an increase in the upper airway inspiratory flow rate; and a treatment means which treats the upper airway flow limitation on detection of said at least one interruption cycle in the upper airway inspiratory flow rate.

In one embodiment, the detection means of the apparatus is adapted to detect a plurality of interruption cycles in the upper airway inspiratory flow rate.

In a further embodiment, the interruption cycle is indicative of an upper airway flow limitation.

In a further embodiment, the detection means detects a decrease in the inspiratory flow rate followed by a subsequent increase in inspiratory flow rate. In this embodiment, the flow rate is interrupted, and the flow rate decreases, followed by a recovery whereupon the flow rate increases before the flow rate finally decreases towards the end of inspiration.

In another embodiment, the subsequent increase in inspiratory flow rate increases the inspiratory flow rate to a maxima that is substantially the same as the rate before the decrease in inspiratory flow rate.

In a further embodiment, the subsequent increase in inspiratory flow rate increases the inspiratory flow rate to a maxima that is relatively lesser rate than the rate before the decrease in inspiratory flow rate.

In yet a further embodiment, the subsequent increase in inspiratory flow rate increases the inspiratory flow rate to a maxima that is relatively greater rate than the rate before the decrease in inspiratory flow rate.

In a still further embodiment, the detection means is adapted to detect the occurrence of at least two or more interruption cycles in the upper inspiratory flow rate and the treatment means treats the airway limitation on detection of said at least two interruption cycles.

In another embodiment, the apparatus is used in the treatment of hypertension caused by pre-eclampsia. In this embodiment, the interruption to inspiratory flow rate is indicative of an upper airway flow limitation which can lead to pre-eclampsia induced hypertension. The type of interruption cycle detected may not be observed in a breathing pattern of a patient suffering from another form of airway limitation such as snoring or sleep apnea. While there is still an inspiratory airway flow limitation in a patient suffering from another form of airway limitation, the increase in airway flow following a decrease in airway flow is not observed. Instead, the inspiratory flow rate continues to decrease at a certain rate until inspiration ends and expiration begins.

In a further embodiment of the first aspect of the invention, the detection means includes a means for measuring vibrations in a patient's airway. Preferably, the detection means to detect the at least one interruption cycle further includes an identification means for identifying those measured airway vibrations which are indicative of the upper airway flow limitation.

In a further embodiment, the measured vibrations in the patient's airway indicative of upper airway flow limitation are caused by a decrease in the diameter of the airway followed by a subsequent increase in the diameter of the airway.

In another embodiment, the subsequent increase in diameter of the airway increases the diameter to substantially the same diameter as before the decrease in diameter of airway.

In a further embodiment, the subsequent increase in diameter of the airway increases the diameter to a diameter less than the diameter before the initial decrease in diameter of the airway.

In a further embodiment, the subsequent increase in diameter of the airway increases the diameter to a diameter greater than the diameter before the initial decrease in diameter of the airway.

In a second aspect, the present invention consists in an apparatus when used in the treatment of hypertension caused by pre-eclampsia, the apparatus including:

a flow rate measurement means which measures an air flow intake rate in an airway of a patient; and a treatment means which treats an upper airway flow limitation in the patient when the measured air flow intake rate falls below a pre-determined flow rate to alleviate hypertension caused by pre-eclampsia.

In a third aspect, the present invention consists in an apparatus for the treatment of hypertension caused by pre-eclampsia, the apparatus including:

a measuring means for measuring airway vibrations in a patient;

an identification means which identifies those measured airway vibrations which are indicative of an upper airway flow limitation; and a treatment means which treats the upper airway flow limitation in the patient.

In one embodiment of the third aspect, the apparatus is used for the treatment of hypertension caused by pre-eclampsia.

In a fourth aspect, the present invention consists in a method of treating an upper airway flow limitation in a patient including the steps of:

detecting at least one interruption cycle in an upper airway inspiratory flow rate of the patient wherein the interruption cycle is characterised by a decrease in upper airway inspiratory flow rate followed by an increase in the upper airway inspiratory flow rate; and treating the upper airway flow limitation on detection of an interruption cycle in the upper airway inspiratory flow rate.

In one embodiment of the fourth aspect of the invention, the detecting step comprises detecting a plurality of interruption cycles in the upper airway inspiratory flow rate.

In a further embodiment of the fourth aspect of the present invention, the method is used to treat hypertension caused by pre-eclampsia.

In a fifth aspect, the present invention consists in a method of treating a patient for hypertension caused by pre-eclampsia, the method including the steps of:

measuring an air flow intake rate in an airway of the patient; and treating an upper airway flow limitation in the patient when the measured air flow intake rate falls below a pre-determined flow rate to alleviate hypertension caused by pre-eclampsia.

In a sixth aspect, the present invention consists in a method of treating a patient for an upper airway flow limitation, the method including the steps of:

measuring airway vibrations in the patient;

identifying those measured airway vibrations which are indicative of the upper airway flow limitation;

on identification, treating the upper airway flow limitation in the patient.

In one embodiment of the sixth aspect, the method is used to treat hypertension caused by pre-eclampsia.

The inventor has observed that women with pre-eclampsia exhibit substantial blood pressure elevations during sleep even when medicated following current medical practice to control blood pressure. The present invention results from the inventor's observation that there is upper airway flow limitation (in the absence of apnea) in the majority of these patients. As mentioned above, upper airway vibration is well known in snoring, where the base frequency of flutter is usually above 30 Hz. However, in pre-eclamptic women, the upper airway often has a much lower vibration frequency, with a base frequency of flutter in the range of about 0.2 to about 10 Hz (typically about 1-2 Hz).

Whereas these women on occasions may also produce audible snoring (which would be recognised by an observer) the low frequency vibrations are not audible, and would not be detected by commonly used sleep and breathing recordings, thus failing to reveal the upper airway functional abnormality. The inventor has found that this type of low frequency vibrations is representative of an upper airway flow limitation which is the cause of increasing blood pressure in sleeping patients with pre-eclampsia, likely through the effect of the limitation of reducing ventilation and increasing arterial carbon dioxide.

As noted in the background, the only cure for pre-eclampsia is delivery of the baby and placenta. This invention does not claim to prevent or treat pre-eclampsia but aims to minimise hypertension that is present due to the pre-eclampsia. As such, at least some embodiments of this invention may be used as an additional tool by clinicians treating patients with pre-eclampsia.

In one embodiment of the first, second and third aspects, the treatment means is a device which applies Continuous Positive Airway Pressure (CPAP), more preferably nasal-Continuous Positive Airway Pressure (nCPAP), to the airway of the patient. In another embodiment of the apparatus, the treatment means is a device which induces positive airway pressure therapy.

In another embodiment, the flow rate measurement means and the treatment means may be constructed together as part of one apparatus, such as the AutoSet product from ResMed described in U.S. Pat. No. 5,245,995, the contents of which are incorporated herein by reference. This apparatus senses and responds to airway flow limitations and, once appropriately modified, could be used to sense an upper airway flow limitation characterised by at least one decrease in upper airway inspiratory flow rate followed by at least one increase in flow rate.

In a further embodiment, the treatment means may operate with two modes of delivery, a first mode for use when the patient is awake, and a second mode for use when the patient is asleep. In the first mode of air delivery, the treatment means provides a minimally intrusive air and pressure delivery to the patient, and hence is more comfortable. In the second mode of air delivery, the treatment means provides a relatively greater air and pressure delivery to the patient than in the first mode, which is sufficient to treat an air flow limitation.

In another embodiment, the treatment means may additionally include a sleep sensor which senses whether or not the patient is asleep, and may also include a switching means which responds to the sleep sensor and automatically switches the treatment means between the two modes of air delivery. This embodiment addresses one of the key issues in treating blood pressure elevations during sleep in women with pre-eclampsia, namely the comfort of CPAP, including nCPAP, or positive airway pressure therapy. This feature is an improvement over the prior art because as soon as the patient goes to sleep (as determined by an appropriate sensing algorithm in the treatment means), the second treatment mode is activated. In the known devices, the second treatment mode is not activated is not activated until the end of the "setting time" period which may lead to the activation of the second treatment mode being delayed beyond that desirable or activated before the patient has in fact gone to sleep.

In a further embodiment, the sleep sensor is adapted to register that the patient is asleep when there is a reduced average airflow in the patient's upper airway. Another embodiment is adapted to register that the patient is asleep when a movement sensor detects a reduced respiration effort by the patient. In another embodiment, known ECG techniques are used for establishing whether the patient is awake or asleep.

In another embodiment, the identification means is adapted to identify airway vibrations in the frequency range of 0.2 to 10 Hz as airway vibrations which are indicative of an upper airway flow limitation.

In a further embodiment, the identification means is adapted to identify airway vibrations in the frequency range of 0.5 to 5 Hz as airway vibrations which are indicative of an upper airway flow limitation.

In another embodiment, the detection means and the identification means are together capable of detecting and generating an output signal representative of the breathing cycle of the patient. A breathing cycle detection and identification means is disclosed in International Application No PCT/AU96/00306, the contents of which are incorporated herein by reference. While the breathing rate of a human can vary significantly due to such factors as illness or exertion, the frequency of the breathing cycle of a sleeping human typically lies in the range of greater than 0 Hz and less than or equal to 2 Hz. The advantage of having the apparatus generate an output signal representative of the breathing cycle is that the airway vibrations indicative of an upper airway flow limitation can be time-locked to the breathing cycle. If peaks in the signal occur during inspiration or expiration, this provides confirmation that the signal being received is in fact due to airway vibrations, rather than from some other source.

In a further embodiment, the apparatus may include a comparator means which compares the signal representative of the breathing cycle with a signal indicative of airway vibrations, and produces an output indicative of the comparison.

In another embodiment, the measuring means which measures airway vibrations may be selected from the group consisting of a pressure detector comprising a piezoelectric transducer and an accelerometer comprising an integrated circuit containing a floating piezoelectric transducer. The pressure or acceleration detector can be placed on or under the mattress of a bed on which the patient will sleep. This arrangement is particularly advantageous as there is no discomfort caused to the patient by the attachment of any sensors. This arrangement also avoids the high risk of detachment or disconnection of sensors attached to the patient during the long hours of sleep. The detector could also be attached to the bed frame or incorporated in a pillow as well as or instead of on or under the mattress. The detector may further be attached to a hearing aid placed in the ear of the patient.

In a further embodiment, the pressure detector can comprise a piezoelectric transducer while the accelerometer can comprise an integrated circuit containing a floating piezoelectric transducer. In a preferred embodiment, the piezoelectric transducer comprises one or a plurality of sheets of piezoelectric plastics material such as polyvinylidene fluoride (hereinafter called PVDF) or an analogue or family derivative thereof. PVDF is an ideal material for this invention as it has a potential frequency response from sub Hertz (ie less than one cycle per second) to kiloHertz levels. In addition, the material is highly sensitive, producing relatively larger voltages in response to extremely small movements. It can, for example, act as a highly sensitive microphone detecting low levels of sound pressure. In this invention, the microphone property of PVDF is used to essentially "listen" to the vibrations of the patient's airway. This embodiment takes advantage of the physical properties of this plastic, which is robust, to characterise the vibration of the airway, and preferably the breathing cycle of the patient, to identify the dominant frequency components of these actions and, by comparison, to positively separate each action thus allowing the generation of electrical signals which can be recorded and identified as that of the vibration of the airway and breathing movements.

In yet a further embodiment, the piezoelectric plastics material may consist of a layer of this material attached to a firm rubber or plastic backing sheet, with or without an air space. Multiple layers of the piezoelectric material throughout a mattress may also be utilised where appropriate.

In another embodiment, the detector detects movements of low frequency (e.g. about 0-5 Hertz) which can be digitally processed and amplified to give a signal representative of the breathing cycle (inspiration and expiration) of the patient. The detector will be able to detect sub-audible vibrations of the patient's airway which may also be digitally processed and amplified to give a signal representative of the sub-audible vibrations in the airway.

BRIEF DESCRIPTION OF THE DRAWINGS

The following description of a preferred embodiment of the present invention is provided as an example of the invention and is described with reference to the accompanying drawings in which.

DETAILED DESCRIPTION OF THE DRAWINGS

Figure 1:
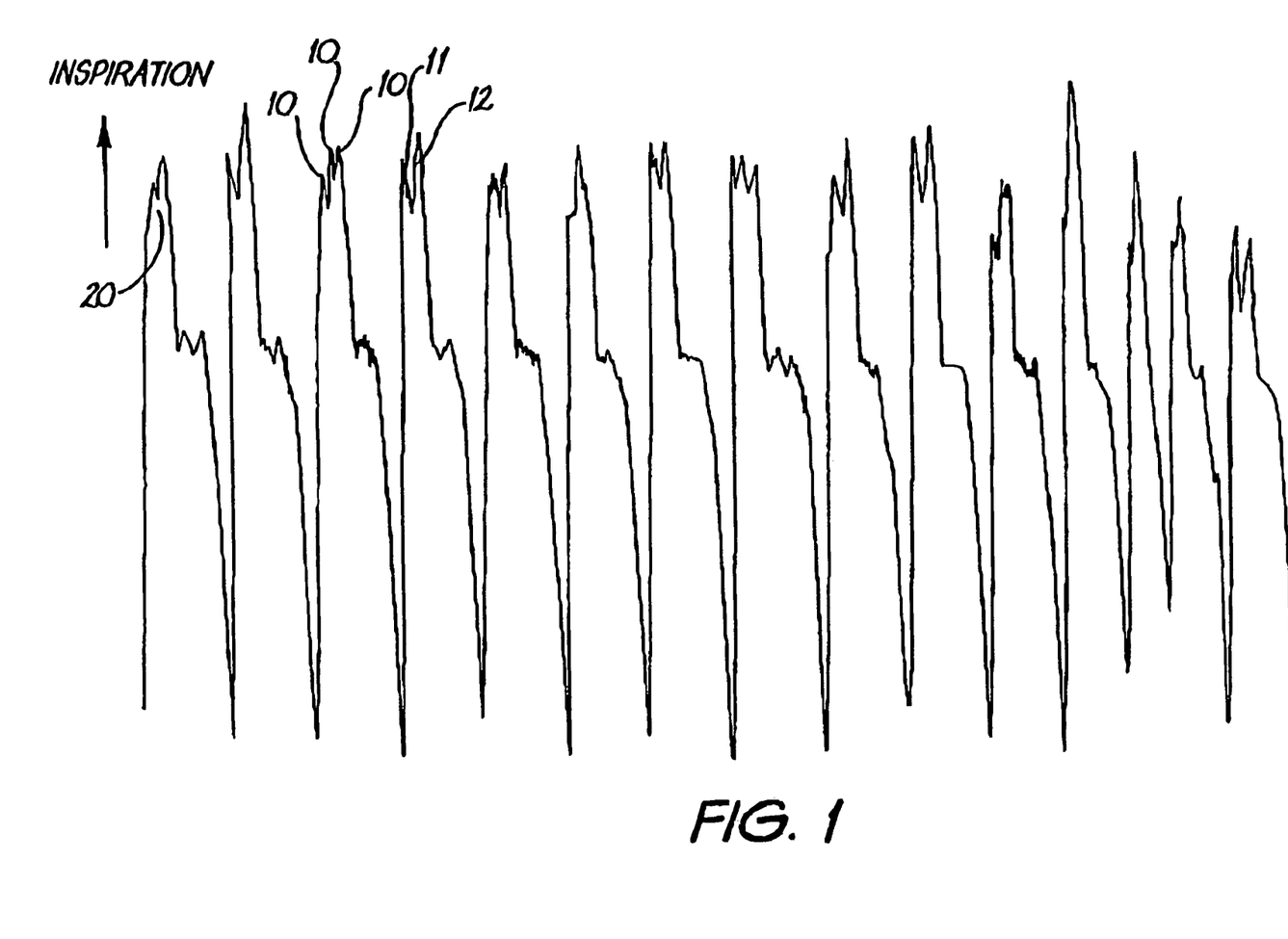
FIG. 1 is a graph of the breathing cycle of a patient with pre-eclampsia.

FIG. 1 is a graph of the breathing cycle of a patient with pre-eclampsia. Small interruptions to inspiratory flow 10 superimposed at the peak 20 of each cycle are indicative of an upper airway flow limitation, not usually associated with audible snoring. In each case, the interruption 10 comprises at least a first decrease 11 in the inspiratory flow rate and a subsequent increase 12 in inspiratory flow rate. In this way, the flow rate is interrupted, followed by a "recovery" before finally decreasing towards the end of inspiration.

The small interruptions 10 in inspiratory flow are not observed in the breathing patterns of a patient suffering from snoring in which case whilst there is still a flow limitation, there is no "recovery" of flow rate as observed in a patient with pre-eclampsia.

Figure 2:
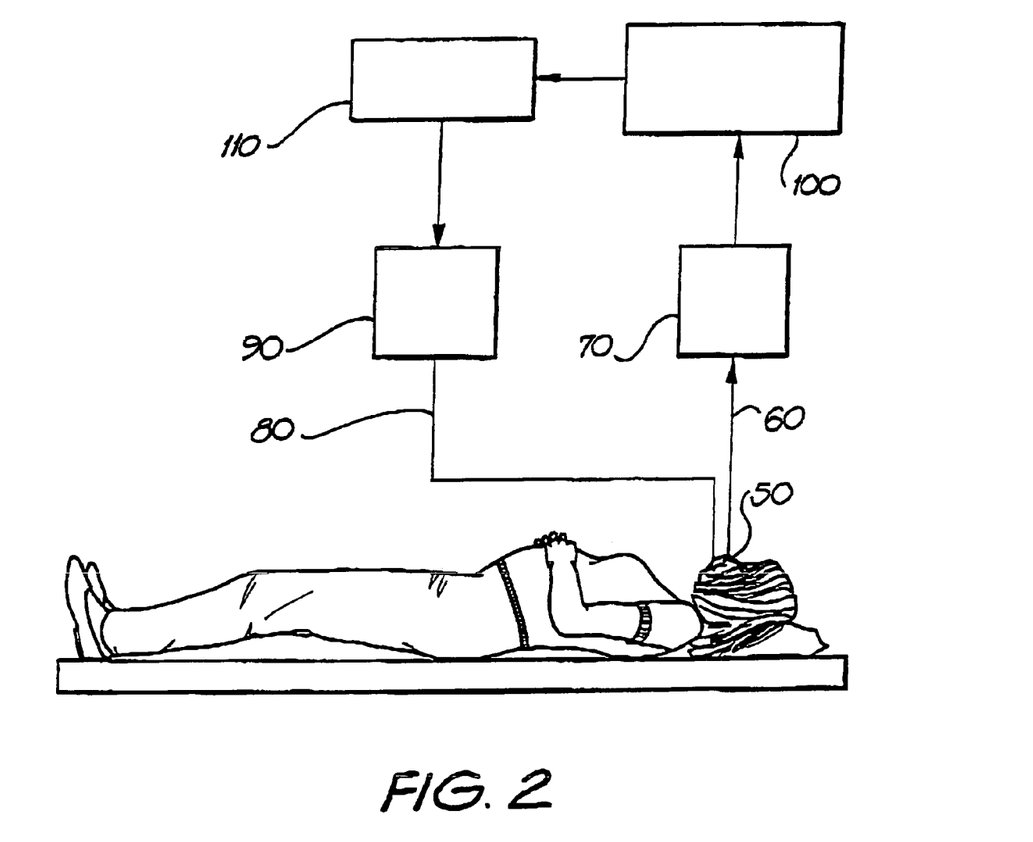
FIG. 2 is a schematic representation of an embodiment of an apparatus for treating a patient with hypertension caused by pre-eclampsia.

FIG. 2 shows a patient 30 being treated for hypertension caused by pre-eclampsia. The patient 30 is laying on a bed 40, and has a mask 50 covering the nose. The mask 50 is shown connected by 80 to a nasal-Continuous Positive Airway Pressure (nCPAP) apparatus 90. The flow rate measurement means 70 detects the rate at which the patient breathes in air, and generates a signal which is sent to a central controller 100. When the flow rate measurement means 70 detects the interruptions to inspiratory flow 10, the controller 100 activates a switch 110 which activates the nCPAP apparatus 90 to supply air to the patient 30 at a pressure which ameliorates or eliminates the upper airway flow limitation for that patient.

In another embodiment of the invention when the flow rate measurement means 70 detects that the flow rate has fallen below a present level, the controller 100 activates the nCPAP apparatus 90 to supply air to the patient 30 at a pressure which ameliorates or eliminates the upper airway flow limitation. When the flow rate measurement means 70 detects that the flow rate increases above the preset level, the controller activates the switch 110 to switch the nCPAP apparatus 90 into a mode in which a reduced air pressure is applied to the patient's airways. The patient is assumed to be awake in this mode.

Figure 3:
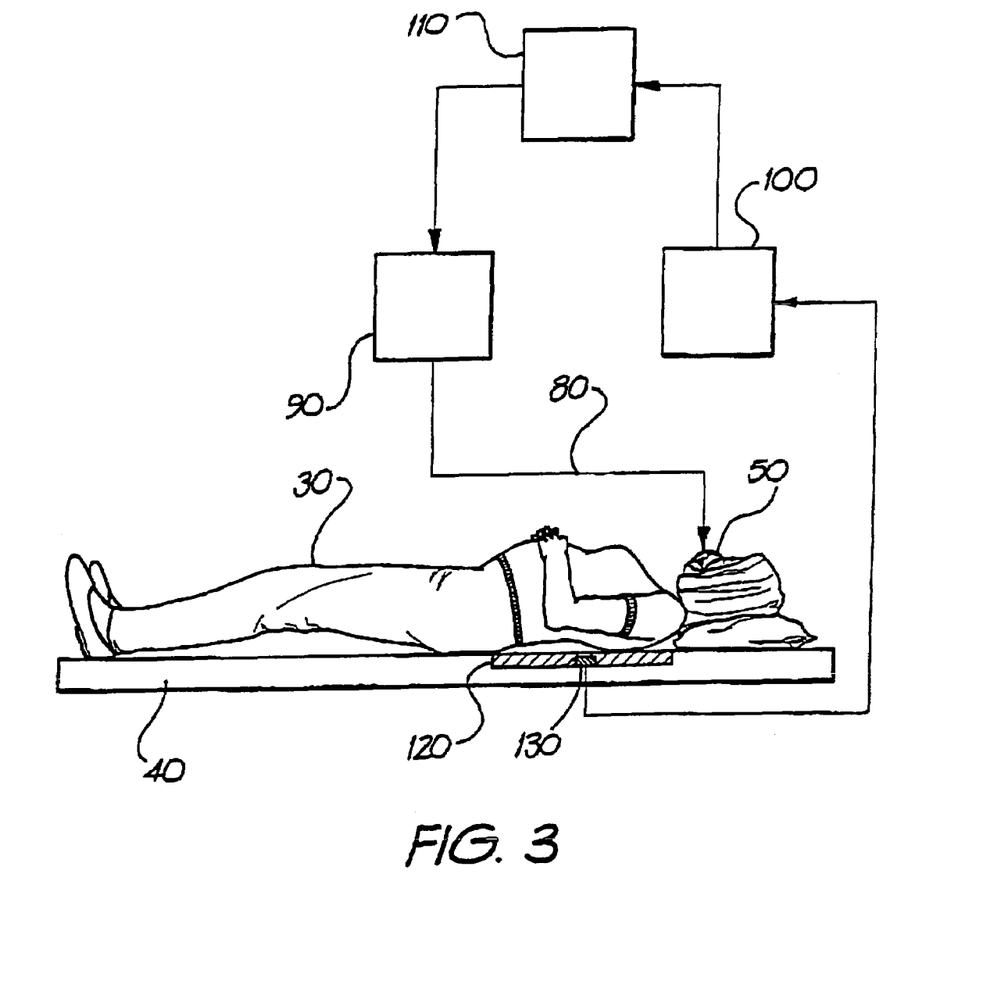
FIG. 3 is a schematic representation of another embodiment of an apparatus for treating a patient with hypertension caused by pre-eclampsia.

FIG. 3 shows another embodiment of an apparatus for treating a patient 30 for hypertension caused by pre-eclampsia. The same reference numerals are used where the features are the same as in FIG. 2. This embodiment uses a mat 120 with a measuring means 130 beneath the patient 30 to measure airway vibrations of the patient. When airway vibrations are detected and determined to be representative of at least one interruption cycle, a signal is sent to the controller 100. The controller 100 then activates the switch 110, which switches on the nCPAP apparatus 90. The nCPAP apparatus 90 then supplies air to the patient 30 at a pressure which ameliorates or eliminates the upper airway flow limitation for that patient.

Figure 4:
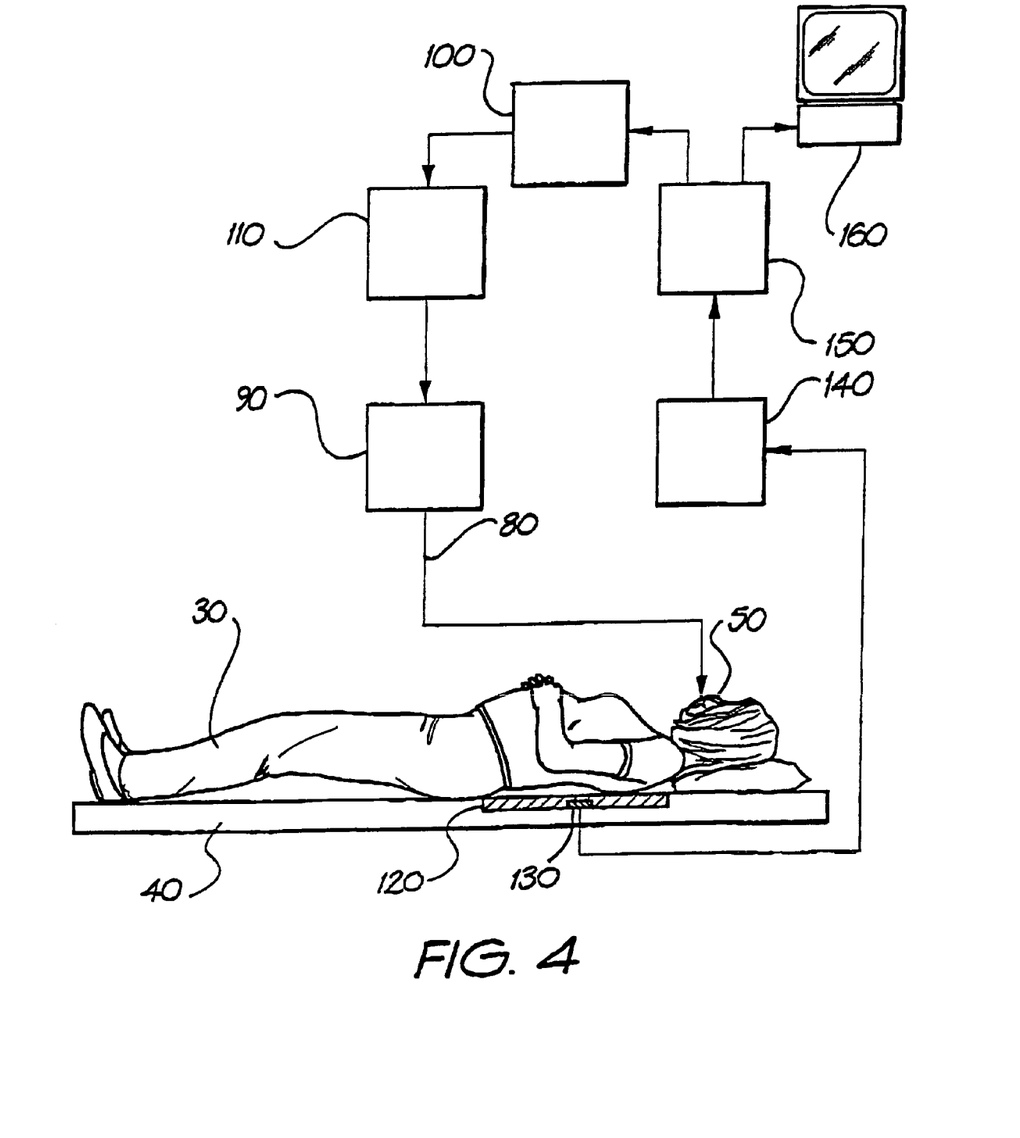
FIG. 4 is a schematic representation of a further embodiment of an apparatus for treating a patient with hypertension caused by pre-eclampsia.

FIG. 4 depicts a further embodiment of the invention wherein, mat 120, having measuring means 130, is placed beneath the patient 30 to measure airway vibrations in the patient. The measuring means 130 is connected by appropriate electrical leads to an electronic amplifier device 140. The amplified signals are then passed to a comparator 150 which is adapted to discriminate from the signals output from the measuring means 130 signals representative of the breathing cycle of the patient and of episodes of airway vibrations which are representative of at least one interruption cycle. The amplified signals from the comparator can be fed to a display means 160 or fed directly to controller 100. The controller 100 activates switch 110 which activates the nCPAP apparatus 90 to supply air to the patient 30 at a pressure which ameliorates or eliminates the upper airway flow limitation for that patient.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An apparatus for the treatment of an upper airway flow limitation in a patient, the apparatus including:
   (a) a means to detect at least one interruption cycle in an upper airway inspiration flow rate of the patient wherein the interruption cycle is characterized by a decrease in upper airway inspiratory flow rate followed by an increase in the upper airway inspiratory flow rate; and
   (b) a treatment means which treats the upper airway flow limitation on detection of said at least one interruption cycle in the upper airway inspiratory flow rate.

2. The apparatus of claim 1 wherein the detection means is adapted to detect a plurality of interruption cycles.

3. The apparatus of claim 1 when used in the treatment of hypertension caused by pre-eclampsia.

4. The apparatus of claim 1 wherein the means to detect the at least one interruption cycled includes a means for measuring vibrations in a patient's airway.

5. The apparatus of claim 4 wherein the means to detect the at least one interruption cycle further includes a means for identifying those measured airway vibrations which indicate an upper airway flow limitation.

6. The apparatus of claim 1 wherein the means to detect the at least one interruption cycle includes a flow rate measurement means which measures the air flow intake rate in the airway of the patient.

7. The apparatus of claim 1 wherein the treatment means is a device which applied continuous positive airway pressure to the airway of the patient.

8. An apparatus for the treatment of hypertension caused by pre-eclampsia, the apparatus including:
   (a) a flow rate measurement means which measures an air flow intake rate in an airway of a patient;
   (b) a means to detect at least one interruption cycle in an upper airway inspiration flow rate of the patient wherein the interruption cycle is characterized by a decrease in upper airway inspiratory flow rate followed by an increase in the upper airway inspiratory flow rate; and
   (c) a treatment means which treats an upper airway flow limitation in the patient in response to detecting an interruption cycle in the air flow intake rate, said interruption cycle characterized by a decrease in the air flow intake rate followed by an increase in the airflow intake rate so as to alleviate hypertension caused by pre-eclampsia.

9. An apparatus for the treatment of hypertension caused by pre-eclampsia, the apparatus including:
   (a) a measuring means for measuring airway vibrations in the patient;
   (b) identification means which identifies those measured airway vibrations which are indicative of an interruption cycle in an upper airway;
   (c) a means to detect at leas one interruption cycle in an upper airway inspiration flow rate of the patient wherein the interruption cycle is characterized by a decrease in upper airway inspiratory flow rate followed by an increase in the upper airs ay inspiratory flow rate; and (d) treatment means which treats the upper airway flow limitation in the patient upon detection of the interruption cycle.

10. The apparatus of claim 9 when used for the treatment of hypertension caused by pre-eclampsia.

11. The apparatus of claim 9 wherein airway vibrations in the frequency range of about 0.2 to about 10 Hz are identified by the identification means as indicative of the upper airway flow limitation.

12. The apparatus of claim 9 wherein airway vibrations in the frequency range of about 0.5 to about 5 Hz are identified by the identification means as indicative of the upper airway flow limitation.

13. The apparatus of claim 9 wherein the identification means is capable of generating a signal representative of the breathing cycle of the patient.

14. The apparatus of claim 13 wherein the identification means includes a comparator means which compares the signal representative of the breathing cycle with a signal representative of the airway vibrations and produces an output signal representative of the comparison.

15. The apparatus of claim 9 wherein the measuring means is selected from the group consisting of a pressure detector comprising a piezoelectric transducer and an accelerometer comprising an integrated circuit containing a floating piezoelectric transducer.

16. The apparatus of claim 15 wherein the pressure detector or accelerometer is placed on or under a bed on which a patient sleeps.

17. The apparatus of claim 16 wherein a further pressure detector or accelerometer is attached to the bed frame or incorporated into a pillow.

18. The apparatus of claim 15 wherein the pressure detector or accelerometer is attached to a hearing aid placed in an ear of the patient.

19. The apparatus of claim 15 wherein the measuring means is a pressure detector comprising a piezoelectric transducer and further wherein the pressure detector comprises one or a plurality of sheets of piezoelectric plastic material.

20. The apparatus of claim 19 wherein the piezoelectric plastic material is attached to a firm rubber or plastic backing sheet.

21. The apparatus of claim 19 or 20 wherein the pressure detector detects both sub-audible vibrations of the patient's airway and low frequency movements of the breathing cycle of the patient.

22. The apparatus of claim 1, claim 8 or claim 9 wherein the treatment means has two modes of treatment, a first treatment mode when the patient is awake and a second treatment mode when the patient is asleep.

23. The apparatus of claim 22 herein, in the first treatment mode, a relatively minimally intrusive continuous positive airway pressure is delivered to the airway of the patient.

24. The apparatus of claim 22 wherein, in the second treatment mode, a relatively higher continuous positive airway pressure is delivered to the airway of the patient than in the first treatment mode, the continuous positive airway pressure being set so as to be sufficient to treat the upper airway flow limitation in the patient.

25. The apparatus of claim 22 wherein the treatment means further includes a sleep sensor which determines whether the patient is asleep or awake.

26. The apparatus of claim 25 wherein the sleep sensor emits a signal upon sensing whether the patient is asleep or upon sensing that the patient is awake.

27. The apparatus of claim 26 wherein the treatment means further includes a switching means and whereupon receiving a signal from the sleep sensor, the switching means causes the treatment means to switch from one treatment mode to the other treatment mode.

28. The apparatus of claim 25 wherein the sleep sensor senses that the patient is asleep when there is a reduced average airflow into the airway of the patient.

29. The apparatus of claim 28 wherein the sleep sensor further includes a movement detector which detects the respiration effort in the patient.

30. The apparatus of claim 29 wherein the sleep sensor senses that the patient is asleep when there is a reduced respiration effort in the patient.

31. The apparatus of claim 25 wherein the sleep sensor includes an electrocardiograph.

32. A method of treating an upper airway flow limitation in a patient including the steps of:
  (a) detecting at least one interruption cycle in an upper airway respiratory flow rate of the patient wherein the interruption cycle is characterized by a decrease in upper airway inspiratory flow rate followed by an increase in the upper airway inspiratory flow rate; and
  (b) treating the upper airway flow limitation on detection of an interruption cycle in the upper airway inspiratory flow rate.

33. The method of claim 32 wherein the detecting step comprises detecting a plurality of interruption cycles in the upper airway inspiratory flow rate.

34. The method of claim 32 or claim 33 wherein hypertension caused by pre-eclampsia is treated.

35. A method of treating a patient for hypertension caused by pre-eclampsia, the method including the steps of: measuring an air flow intake rate in an airway of the patient in response to an interruption cycle in the air flow intake rate, said interruption cycle characterized by a decrease in the airflow intake rate followed by an increase in the airflow intake rate so as to alleviate hypertension caused by pre-eclampsia.

36. A method of treating a patient for hypertension caused by pre-eclampsia, the method including the steps of:
  (a) measuring airway vibrations in the patient;
  (b) identifying those measured airway vibrations which are indicative of an interruption cycle in an upper airway, where the interruption is characterized by a decrease in upper airway inspiratory flow rate followed by an increase in the upper airway inspiratory flow rate; and
  (c) on identification of the interruption cycle in an upper airway, treating the upper airway flow limitation in the patient.

37. The method of claim 36 wherein airway vibrations identified in the frequency range of about 0.2 to about 10 Hz are taken as indicative of the upper airway flow limitation.

38. The method of claim 36 wherein airway vibrations identified in the frequency range of about 0.5 to about 5 Hz are taken as indicative of the upper airway flow limitation.

39. The method of claim 36 further including a step of identifying movements indicative of the breathing cycle of the patient.

40. The method of claim 39 further including the step of comparing movements indicative of the breathing cycle with the measured airway vibrations.

41. The method of claim 32 or 35 or 36 wherein the step of treating the upper airway flow limitation includes applying continuous positive airway pressure to the airway of the patient.

42. The method of claim 41 wherein the step of treating the patient is carried out in two modes, a first treatment mode when the patient is awake and a second treatment mode when the patient is asleep.

43. The method of claim 42 further including the step of determining whether the patient is asleep or awake.

44. The method of claim 43 further including the step of switching between the two modes of treatment upon determining whether the patient is asleep or awake.

45. The method of claim 44 wherein whether the patient is asleep or awake is determined by the average airflow into the airway of the patient and further wherein a reduced average airflow in the airway of the patient indicates that the patient is sleeping.

46. The method of claim 43 wherein whether the patient is asleep or awake is determined by the respiration effort of the patient and further wherein a reduced respiration effort indicates that the patient is asleep.

47. The method of claim 43 wherein whether the patient is awake or asleep is determined by analysis of an electrocardiogram of the patient.

* * * * *